United States Patent
Kroll

[11] Patent Number: 6,101,414
[45] Date of Patent: Aug. 8, 2000

[54] METHOD AND APPARATUS FOR ANTITACHYCARDIA PACING WITH AN OPTIMAL COUPLING INTERVAL

[75] Inventor: Mark W. Kroll, Simi Valley, Calif.

[73] Assignee: Pacesetter, Inc., Sylmar, Calif.

[21] Appl. No.: 09/021,753

[22] Filed: Feb. 11, 1998

[51] Int. Cl.[7] .................................................. A61N 1/365
[52] U.S. Cl. .................................................. 607/14; 607/5
[58] Field of Search ................................. 607/9, 14, 25, 607/4, 5

[56] References Cited

U.S. PATENT DOCUMENTS

| | | | |
|---|---|---|---|
| 4,830,006 | 5/1989 | Haluska et al. | 607/9 |
| 5,431,689 | 7/1995 | Weinberg et al. | 607/14 |
| 5,601,609 | 2/1997 | Duncan | 607/5 |
| 5,709,710 | 1/1998 | Armstrong | 607/5 |

*Primary Examiner*—Jeffrey R. Jastrzab

[57] ABSTRACT

An implantable defibrillator includes a coupling interval generator for defining a coupling interval as a dynamic function of the VT interval. The coupling interval is determined based on a nonlinear function so that a more proportionately aggressive therapy is applied with longer VT intervals.

18 Claims, 4 Drawing Sheets

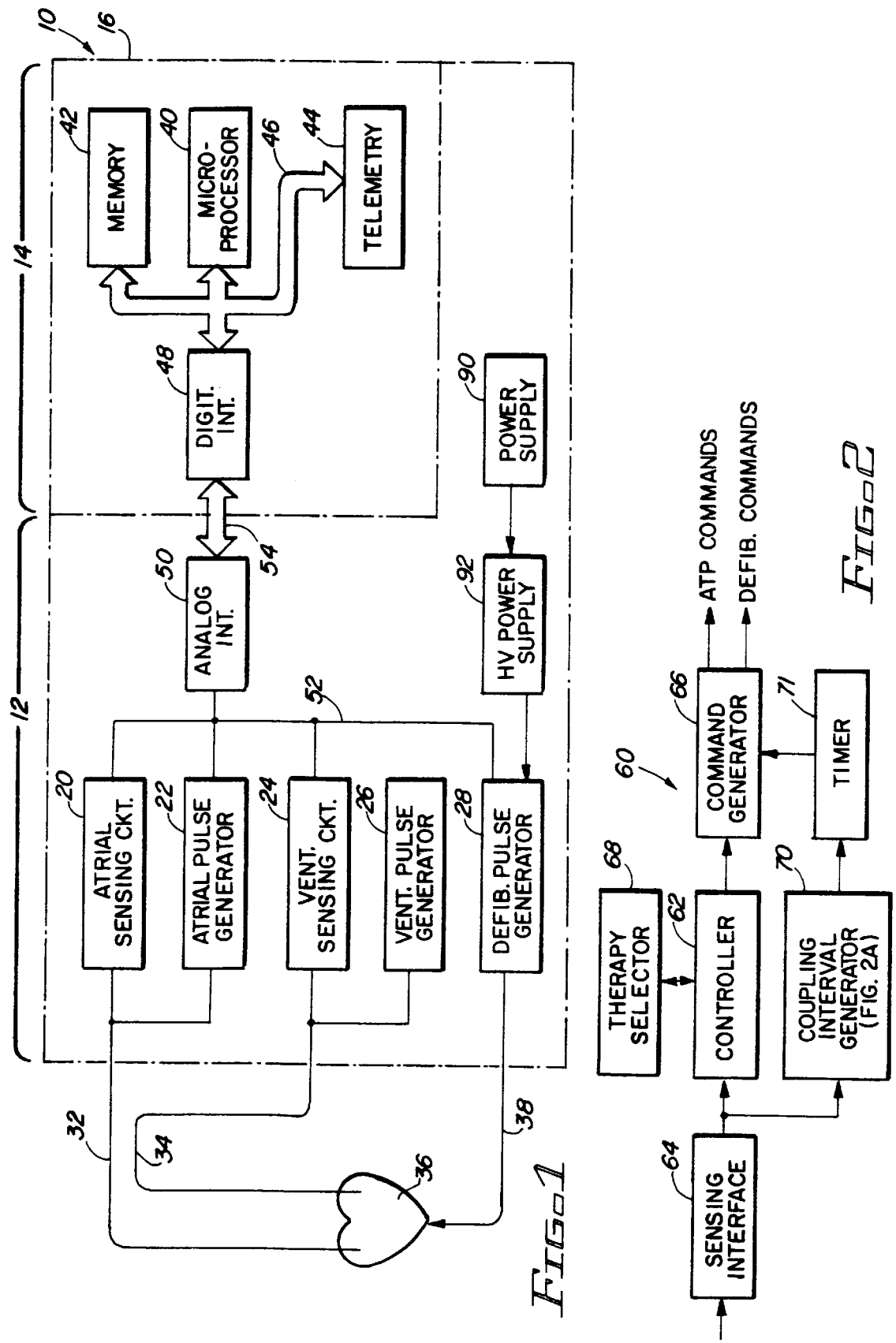

6,101,414

METHOD AND APPARATUS FOR ANTITACHYCARDIA PACING WITH AN OPTIMAL COUPLING INTERVAL

FIELD OF THE INVENTION

This invention relates generally to implantable cardiac stimulating devices used to apply antitachycardia therapy and other therapeutic pulses to a patient's heart in the presence of tachyarrhythmia. More particularly, this invention pertains to an implantable cardioverter/defibrillator and method for timing antitachycardia pacing pulses with respect to the intrinsic cardiac beats to insure rapid and safe reversion to a normal sinus rhythm thereby preventing acceleration of the arrhythmia.

BACKGROUND OF THE INVENTION

After extensive research and development, practical implantable cardioverter/defibrillators are now available for the medical community which can be used to effectively control tachyarrhythmia such as ventricular and/or atrial tachycardia as well as fibrillation. Preferably these devices are associated with, and in fact, incorporate a stimulation device that also provides bradycardia support.

Typically, an implantable cardioverter/defibrillator (hereinafter referred to simply as "defibrillator") monitors the patient's cardiac function for arrhythmia. Once arrhythmia is detected, the defibrillator analyzes and classifies the condition of the heart. For example, based on the rate of the ventricular beats and other factors, the patient's condition may be identified as low-rate tachycardia, high-rate tachycardia or fibrillation. The defibrillator then provides therapy specifically selected for the identified condition. The present invention pertains to therapy applied in response to tachycardia, and more particularly to therapy involving application of pacing pulses, and commonly referred to as antitachycardia pacing or ATP.

ATP consists of a three-step process used to revert the heart to normal sinus. First, ventricular tachycardia (VT) is detected and its interval (the VT interval) is determined. Second, a coupling interval is determined. Third, a delay is initiated corresponding to the coupling interval. At the end of the delay cardioversion pacing pulses are applied to the ventricle. The interval, number and frequency of the cardioversion pacing pulses are selected to capture the ventricle.

The selection of the coupling interval of the cardioversion pulses with respect to the intrinsic beats is very important. This interval is usually expressed or defined by a percentage relating the intrinsic ventricular interval and the coupling interval. Prior to the present invention this coupling percentage was defined as a parameter having one of two values. A relatively low coupling percentage was used for tachyarrhythmia of relatively low frequency. At a higher frequency (for example, above a preselected threshold), a higher coupling percentage was used. The result was coupling interval which was relatively longer at higher VT rates and provides proportionately a more aggressive antitachycardia therapy at lower VT rates.

A major problem with the approach described above is that the coupling percentage is initially set to at most one or two values, typically selected on implantation by the physician. This approach assumes either that the coupling percentage is not an important parameter and hence one or two values are enough, or that the same value(s) can be used for patients at all times. However, studies have shown that there is no universal optimal percentage but, to the contrary, the optimal percentage may not only vary from patient to patient but also from one VT episode to another even for the same patient.

The present invention addresses this problem and provides a method and apparatus wherein the coupling percentage and/or coupling interval is adjusted automatically on the fly thereby insuring that an optimal coupling percentage is reached rapidly and aggressively before the patient's condition advances to a potentially dangerous vertical fibrillation.

SUMMARY OF THE INVENTION

The present invention is directed toward an implantable stimulation device, such as a cardioverter/defibrillator, in which the coupling interval for antitachycardia pacing is dynamically adjusted with the VT interval so that a more proportionately aggressive therapy is applied with longer VT intervals.

In the preferred embodiment, the coupling percentage is constant in a first range of VT intervals and declines linearly for at least a second range of VT intervals. Stated differently, the coupling percentage will have two zones: one which is relatively constant and a second which dynamically adjusts itself with increasing VT interval.

In a preferred embodiment, the implantable stimulation device constructed in accordance with this invention includes a sensing circuit for sensing intrinsic cardiac activity, a discriminator for classifying the intrinsic cardiac activity into one of a normal sinus rhythm or a tachycardia, an intrinsic cardiac interval detector; and a coupling interval generator. After a VT is detected by the discriminator, antitachycardia pacing (ATP) is applied. The interval between a specific intrinsic cardiac event and the ATP, known as the coupling interval, is defined by the coupling interval generator.

Importantly, in the present invention, the coupling interval generator defines the coupling interval dynamically as a function of the interval of the intrinsic cardiac activity. The coupling interval decreases in a non-proportional manner as the intrinsic cardiac interval increases. Optionally, as part of its operation, the coupling interval generator first defines a coupling percentage which decreases gradually over a preselected range. The coupling interval is then obtained by multiplying the current VT interval and the coupling percentage. Advantageously, the present invention generates a coupling interval that has a continuous profile and further dynamically adjusts the aggressiveness of therapy as the VT intervals get longer.

BRIEF DESCRIPTION OF THE DRAWINGS

FIG. 1 shows a block diagram of an implantable pacemaker with a defibrillator in accordance with the present invention;

FIG. 2 shows a block diagram of a control circuit for the defibrillator of FIG. 2;

DETAILED DESCRIPTION OF THE INVENTION

Figure 2A:
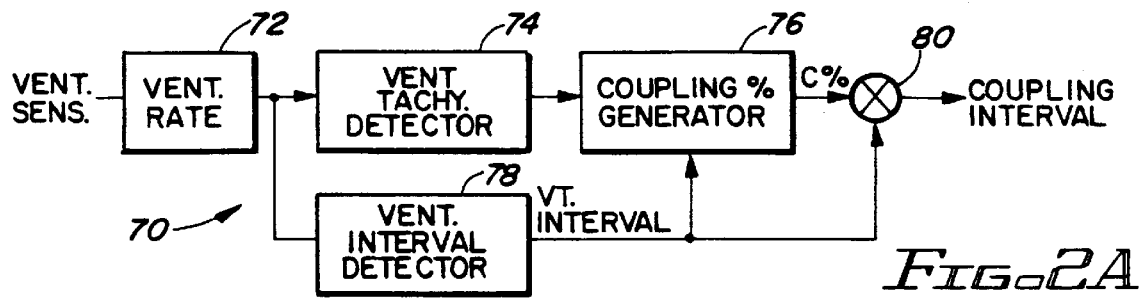
FIG. 2A shows details of the coupling interval generator circuit of FIG. 2 in accordance with this invention.

FIG. 1 shows a block diagram for the preferred embodiment of an implantable stimulation device 10 which incorporates a cardioverter/defibrillator and dual-chamber pacemaker capabilities. However, it should be understood that the present invention could be incorporated into any implantable stimulation device supporting ventricular antitachycardia pacing.

In the illustrated embodiment, implantable stimulation device 10 includes an analog section 12 and a digital section 14 incorporated in a hermetic implantable housing 16. The analog section 12 includes an atrial sensing circuit 20, an atrial pulse generator 22, a ventricular sensing circuit 24, a ventricular pulse generator 26 and a defibrillation pulse generator 28.

Leads 32 and 34 connect the implantable stimulation device 10 to the atrial and ventricular chambers of the heart 36, respectively. The atrial and ventricular sensing circuits (20, 24) are used to sense intrinsic events in the corresponding cardiac chambers, and the atrial and ventricular pulse generators (22, 26) provide respective atrial and ventricular pacing via leads 32 and 34, for example, in a DDD or DDDR mode, well known in the art. Lead 38 is used to deliver defibrillation shocks generated by pulse generator 28. Energy for the implantable stimulation device 10 is provided by a power supply 90. A separate high voltage supply 92 is used to feed the defibrillator pulse generator 28.

The operation of the implantable stimulation device 10 is controlled by the digital section which consists of a microprocessor 40 and a memory 42. The memory 42 holds programming information for the microprocessor 40 and is also used for data logging. Initial programming as well as any programming updates and subsequent downloading of logged data takes place through a telemetry circuit 44. An internal bus 46 couples the memory 42, microprocessor 40 and telemetry circuit 44 together and to a digital section interface 48. Similarly, the various elements of the analog section 12 described above are connected to an analog section interface 50 by an internal bus 52. Communication between sections 12 and 14 is established through a bus 54.

FIG. 2 shows details of the control circuit used to control the timing and energy level of the cardioversion/defibrillation pulses. It should be understood that while discrete circuits are shown in this figure (as well as in FIG. 2A), the control circuit is preferably implemented by software in the microprocessor 40. The control circuit 60 includes a controller 62, a sensing interface 64, and a cardioversion/defibrillation command generator 66.

The circuit No. 60 further includes an antitachycardia therapy selector 68, a coupling interval_generator 70, and a timer 71.

In the preferred embodiment, the tachycardia is detected by the ventricular sensing circuit 24, which typically provides rate and rate stability information to the control circuit 60. However, other physiologic cardiac sensors may also be used to detect the tachycardia (e.g., cardiac output, blood pressure, stroke volume, etc.).

Briefly, the controller 62 sends commands to the ventricular sensing circuit 24 via interface 64 and receives sense signals indicative of the intrinsic ventricular beats therefrom. Using this information and a particular antitachycardia therapy defined by selector 68, the controller then sends control signals to the command generator 66. The command generator 66 then generates commands for generating either antitachycardia pacing signals, or, if necessary, defibrillation pulses, as discussed in more detail below. The timing of these stimulation pulses is determined by timer 71, which is selectably adjusted by the coupling interval, when appropriate, as determined by coupling interval generator 70.

Referring now to FIG. 2A, the coupling internal generator 70 includes a ventricular rate detector 72, a ventricular tachycardia (VT) detector 74, a coupling percentage generator 76, a ventricular interval detector 78, and a multiplier 80. The ventricular rate detector 72 determines the current ventricular rate based on the ventricular cardiac signals from ventricular sensing circuit 24. This ventricular rate is fed to the detector 74 which is used to detect a ventricular tachycardia (VT). Various schemes are known in the art for making such a determination.

Once ventricular tachycardia is detected by detector 74, the coupling percentage generator 76 is initiated, as discussed in more detail below.

Finally, the coupling interval to be determined by generator 70 is related to the ventricular interval associated with the VT. This coupling interval is determined from the heartbeat rate as indicated by rate detector 72. The manner in which the coupling percentage and the corresponding coupling interval is selected will now be described.

As previously discussed, in the prior art, a two-tier scheme has been used to define the coupling percentage. For example, the following ranges may be provided as programmable parameters to the clinicians:

| VT INTERVAL (VTI) | >320 ms | ≦320 ms |
|---|---|---|
| COUPLING % (CP) | 60–75% | 91–97% |

See *IMPLANTABLE CARDIOVERTER DEFIBRILLATOR THERAPY*, by Mark W. Kroll and Michael H. Lehmann, Kluwer Academic Publishers, page 340 (Norwell, Mass.—1996).

Figure 3:
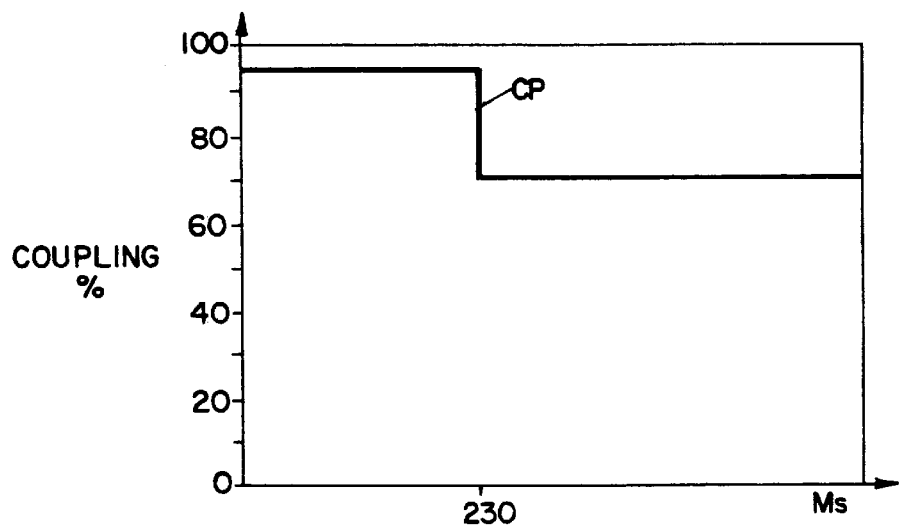
FIG. 3 shows a graph of a prior art two-step method for selecting a coupling percentage.

FIG. 3 shows an example of such a two-tier arrangement in which the coupling percentage (CP) is set to 95% for a VT interval below 320 ms, and 70% for a VT interval above 320 ms.

Figure 4:
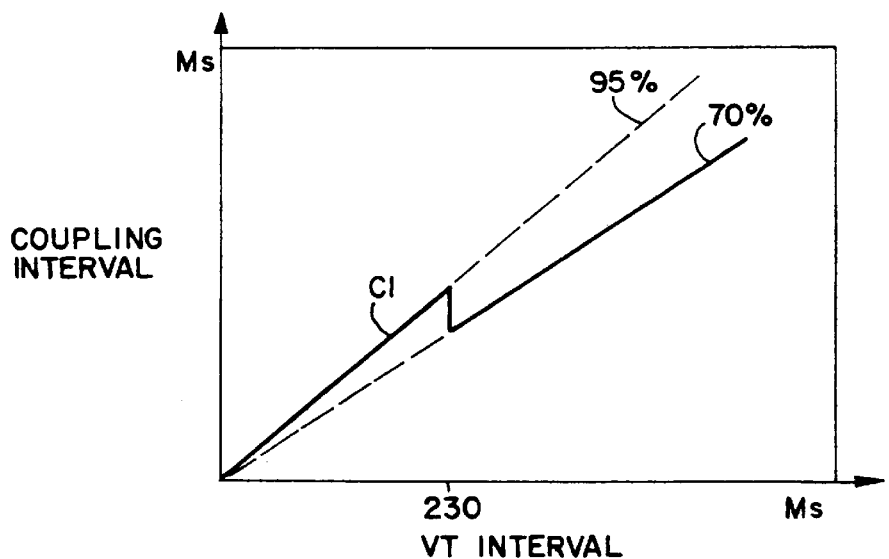
FIG. 4 shows a graph of the coupling interval as a function of the VT interval resulting from the scheme of FIG. 3.

Once the coupling percentage is selected, it can be used to determine the coupling interval. Thus, as shown in FIG. 2A, the multiplier 80 multiplies the current VT interval by the coupling percentage. The coupling interval resulting from FIG. 3 is shown in FIG. 4. As it can be seen in the figure, the coupling interval rises linearly and proportionally with the VT interval until 320 ms, following the 95% curve. At that point, the coupling interval drops to the 70% curve and then continues to rise again linearly and proportionally with the VT interval.

Figure 5:
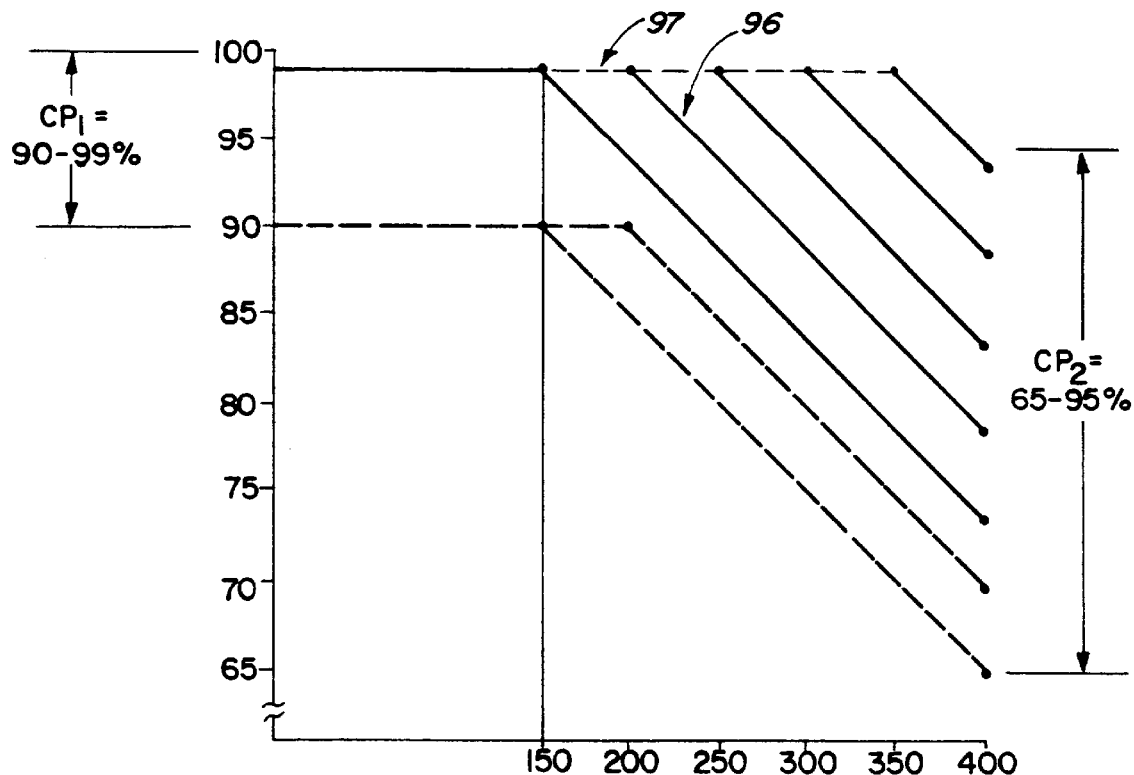
FIG. 5 shows a graph of a method for selecting a coupling percentage in accordance with the present invention.
Figure 6:
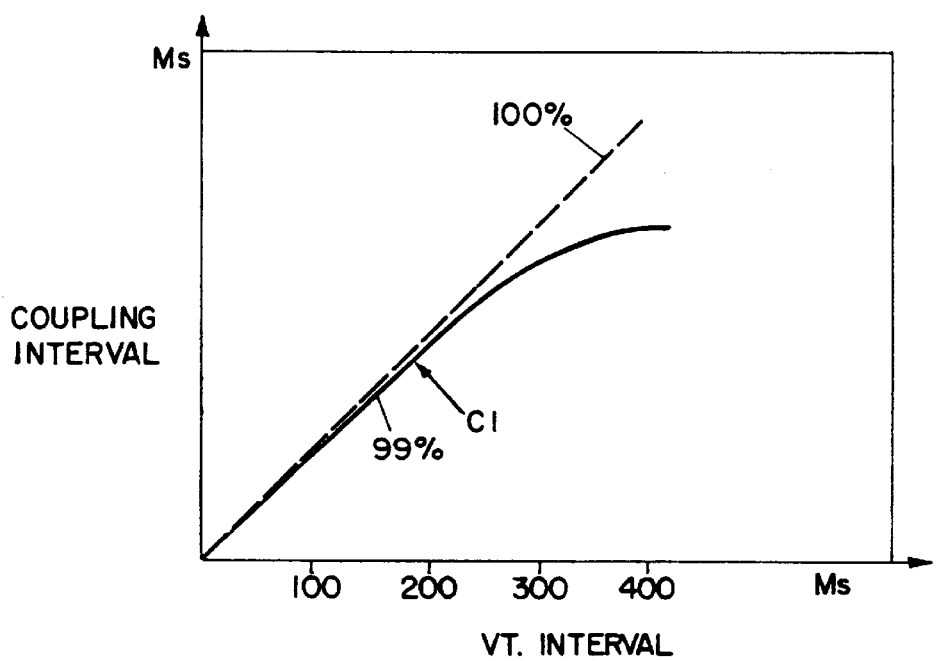
FIG. 6 shows a graph of the coupling interval as a function of the VT interval resulting from the scheme of FIG. 5.

The selection scheme used in the present invention is illustrated in FIGS. 5 and 6. In this scheme, the coupling percentage remains constant until a predetermined level of the VT interval, or breakpoint, after which the coupling percentage drops linearly toward a lower limit.

In other words, the coupling percentage (CP) can be expressed as:

$CP_1 = X(\%)$ for $VTI <= Y$ ms;

$CP_2 = CP_1 - (VTI-Y)/10(\%)$ for $VTI > Y$ ms.

where Y is the predetermined level of the VT interval, or breakpoint, and is preferably a programmable number in the range of 150–400 ms; and where X is a constant in the range of 90–99% for VTI<=Y ms; and X has linearly downward slope in the range of 65–95% for VTI>Y ms.

Additionally, it is within the scope of the invention to modify the slope of the curve for VT intervals greater than the breakpoint by modifying the denominator from "10" to another value.

For example, FIG. 5 shows a plurality of breakpoints (e.g., at 150 ms, 200 ms, 250 ms, etc.), a constant coupling percentage prior to the breakpoints, and the corresponding linearly decreasing curves. Specifically, at 94, the coupling percent remains at 99% until about 200 ms. As the VT interval increases above 200 ms, the coupling percentage drops linearly (at 96) toward a lower limit of 79% as the VT interval increases to 400 ms.

The coupling interval is calculated by multiplying the current VT interval (VTI) with the coupling percentage (CP). Therefore, the coupling interval (CI) as determined in the present invention is given by:

$CI_1 = CP_1*(VTI)/100$(ms) for VTI<=Y ms;
$CI_2 = CP_2*(VTI)/100$(ms) for VTI>Y ms;
which may also be expressed as:
$CI_2 = CI_1 - VTI(VTI-Y)/1000$(ms) for VTI>Y ms.

Figure 7:
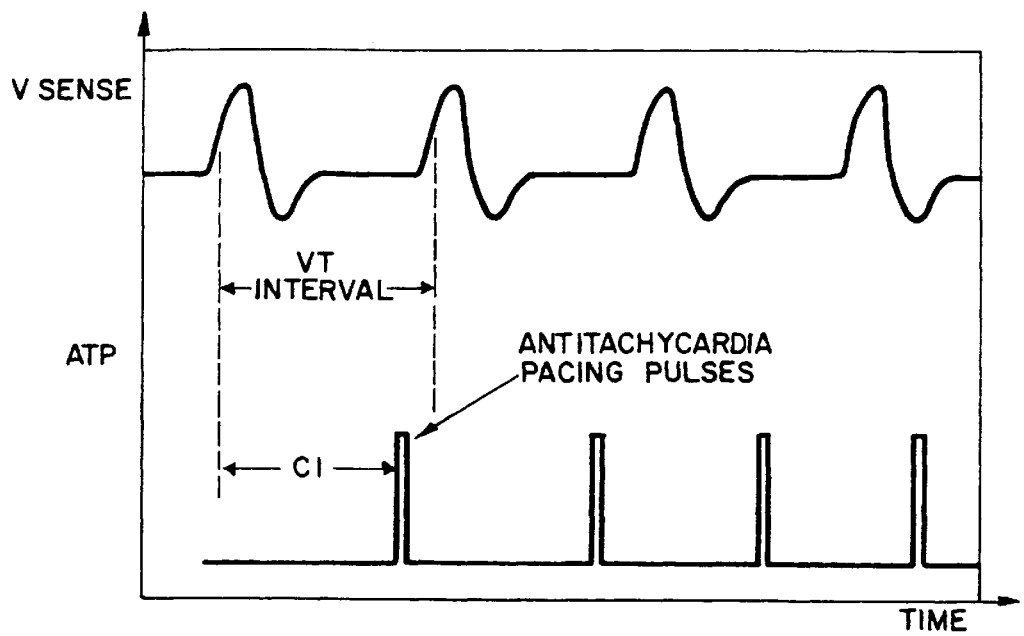
FIG. 7 shows the relationship between ventricular beats and the corresponding antitachycardia pacing pulses generated in accordance with this invention.

The operation of the control circuit as shown in FIGS. 2, 2A, 5 and 6 will now be described in conjunction with the waveshapes of FIG. 7 and the flowchart of FIG. 8.

Figure 8:
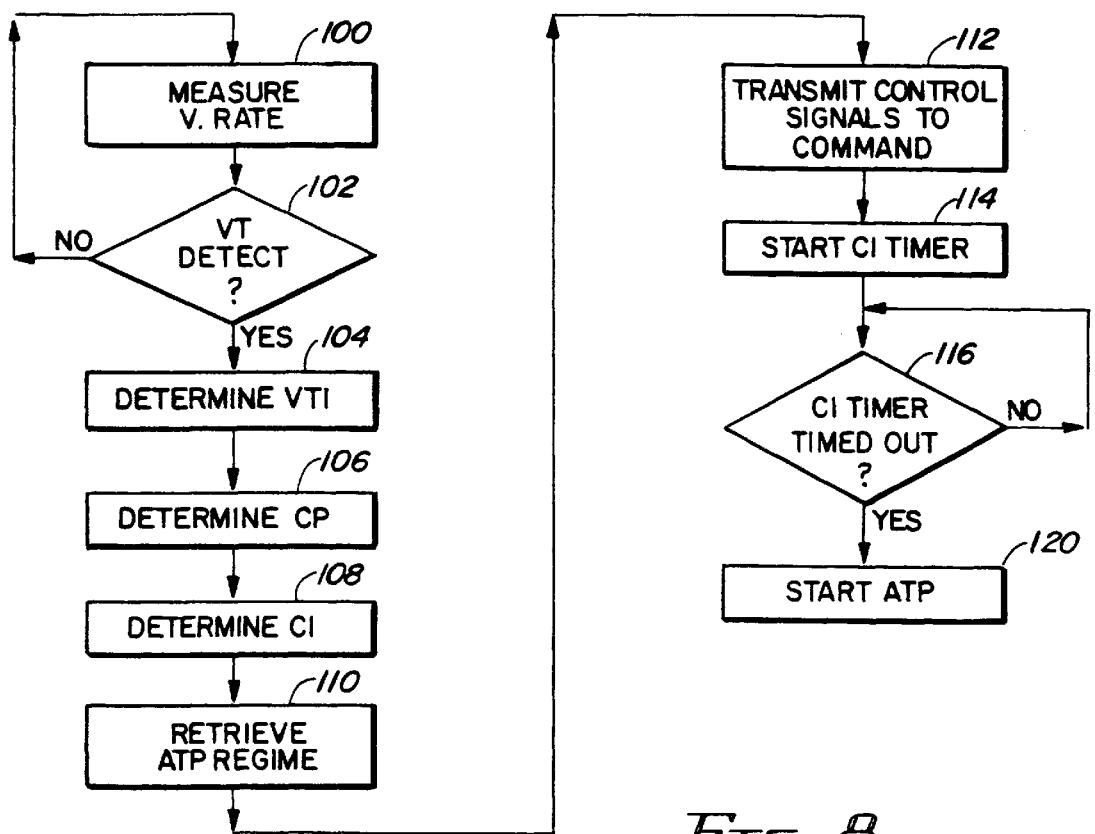
FIG. 8 shows a flow chart demonstrating the operation of the defibrillator of FIGS. 1, 2 and 2A in accordance with the present invention.

In FIG. 8, starting with step 100, the detector 72 measures the current ventricular rate. In step 102, the detector 74 uses this rate and/or other criteria to detect ventricular tachycardia (VT). If in step 102 VT is detected, then in step 104 the corresponding VT interval (VTI) is determined by interval detector 78.

In step 106, the coupling percentage (CP) is determined using, for instance, the nonlinear criteria of FIG. 5. Next, in step 108 the corresponding coupling interval (CI) is determined. (Two discrete steps 106 and 108 are shown to conform to FIG. 2A, which similarly shows two discrete elements 76, 80 to perform these steps. If a microcontroller is used, the two steps 106, 108 could be integrated into a single step and the coupling interval could be either calculated from the formula given above that relates coupling interval to VT interval, or alternatively a look-up table could be used to derive a coupling interval for each VT interval.) Referring momentarily to FIG. 7, the top trace shows a plurality of QRS complexes (or R-waves) for a ventricle undergoing VT. The corresponding VT interval is also indicated in the top trace.

At step 110, the controller 62, in response to the VT condition detected in step 102, retrieves an ATP regime from the ATP selector 68 (FIG. 2). This ATP regime defines a predetermined ATP protocol designed to revert the ventricle to normal rhythm as fast as possible. The regime usually consists of either a pacing pulse or a burst of pacing pulses applied to the ventricle, at a predetermined frequency. Regimes of this kind are described, for example, in See *IMPLANTABLE CARDIOVERTER DEFIBRILLATOR THERAPY*, by Mark W. Kroll and Michael H. Lehmann, Kluwer Academic Publishers, Chapter 16 (Norwell, Mass.— 1996). The intervals between the remaining pacing pulses are related to the basic coupling interval in difference ways depending on the type of ATP regime. For example, with "burst" pacing, all subsequent intervals equal the coupling interval; with "ramp" pacing, they are progressively shorter. The choices between these various regimes is not, however, salient to this invention.

In step 112 the controller 62 transmits control signals to the ATP/defibrillator command generator 66. This generator also receives the coupling interval (CI) determined in step 108.

Importantly, the initiating point for starting ATP is determined by the coupling interval (CI). That is, as shown in FIG. 7, if VT is detected with R-wave "A" then in step 116 command generator 66 starts timer 71 for timing coupling interval (CI) 114. In step 116, a check is performed to see if the timer has timed-out yet. When the timer 71 times-out, the generator 66 issues a command to the ventricular pacing generator to generate pacing pulses commensurate with the ATP previously designated at step 120. The ATP pulses are also shown in FIG. 7.

Another function of the controller 62 is to detect when the ventricle goes into a high rate VT or ventricular fibrillation (VF). This may occur for example if the selected ATP is ineffective. When this condition occurs, either a different ATP regime is selected (e.g., cardioversion), or in case of VF, defibrillation pulses are applied by the defibrillation generator 28.

Thus, the implantable stimulation device described is adapted to provide ATP therapy following a cardiac beat associated with ventricular tachycardia, wherein the coupling interval between the cardiac beat and the ATP therapy is related nonlinearly to the VT interval. This is accomplished by using a method wherein the coupling percentage is not constant for various VT rates or intervals, but is continuously changing. In the specific example given, the coupling percentage declines at a constant slope as the VT interval increases, at least over a portion of the range of VT interval. Obviously other monotonic functions may also be used to relate the coupling percentage to the VT interval, resulting in other nonlinear or non-proportional relationship between the VT interval and the coupling interval.

While the present invention has been described with reference to a particular embodiment and application thereof, numerous other modifications and variations can be made thereto by those skilled in the art without departing from the spirit or the scope of the invention as claimed.

What is claimed is:

1. An implantable cardiac stimulation device arranged and constructed to provide a preselected therapy to a patient's heart in the presence of an arrhythmia, the cardiac device comprising:

a detector that detects pathological tachycardia having a VT interval within a predetermined range;

a coupling interval generator that generates a dynamically adjustable coupling interval based on a non-linear function of the VT interval over at least a predetermined portion of the range so that a more proportionately aggressive therapy is applied as the VT interval gets longer; and a stimulation therapy generator that generates a sequence of stimulation pulses associated with the preselected therapy, the first of the therapy stimulation pulses following a VT interval by the coupling interval.

2. The device of claim 1, wherein the coupling interval generator generates a coupling interval by applying a coupling percentage to a current VT interval.

3. The device of claim 2, wherein the coupling percentage is a programmable curve.

4. The device of claim 3, wherein the coupling percentage is substantially constant over a first portion of the range and varies linearly downward over a second portion of the range, the second portion corresponding to longer VT intervals.

5. The device of claim 4, wherein the coupling percentage is within the range of 65–99%.

6. The device of claim 4, wherein the coupling percentage is between 90–99% over the first portion of the range.

7. The device of claim 4, wherein the coupling percentage is between 65–95% over the second portion of the range.

8. The device of claim 1, wherein:

the predetermined range includes a first portion corresponding to shorter VT intervals and a second portion corresponding to longer VT intervals;

the coupling interval is a proportional function with respect the first portion of the predetermined range; and the coupling interval is a non-proportional function with respect the second portion of the predetermined range.

9. An implantable stimulation device for applying an antitachycardia therapy to a patient's heart, comprising:

sensing means for sensing a cardiac parameter indicative of tachycardia;

detecting means for detecting a VT interval corresponding to the tachycardia;

means for determining a coupling interval non-proportionally related to the VT interval having a continuous profile over a range of VT intervals and which is more aggressive for VT intervals having a longer cardiac cycle; and therapy generator means for generating the antitachycardia therapy, the antitachycardia therapy being applied after a VT interval characteristic of the tachycardia, with the interval between the VT interval and the antitachycardia therapy being defined by the coupling interval.

10. The implantable stimulation device of claim 9, wherein the coupling interval generating means applies a predefined coupling percentage to a current VT interval, the coupling percentage defining a ratio between the coupling interval and the ventricular interval.

11. The implantable stimulation device of claim 10, wherein the ratio is preferably in the range of 65–99%.

12. The implantable stimulation device of claim 10, wherein:

the detecting means detects a tachycardia interval which falls within one of a first range or a second range; and the coupling interval generating means applies a fixed coupling percentage during the first range and a linearly decreasing coupling percentage during the second range.

13. The stimulation device of claim 12, wherein the fixed coupling percentage is between 90–99% during the first range of tachycardia intervals.

14. The stimulation device of claim 12, wherein the fixed coupling percentage is between 65–95% over the second range of tachycardia intervals.

15. An implantable cardioverter/defibrillator applying one of an antitachycardia therapy and a defibrillation therapy to a patient's heart, comprising:

a detector that detects pathological tachycardia having a VT interval within a predetermined range;

a cardiac sensor that senses a cardiac parameter indicative of tachycardia;

a cardiac interval detector that detects a cardiac interval related to the tachycardia within a predetermined range;

a coupling percentage generator that generates a coupling percentage which varies substantially constant over a first portion of the range and varies linearly downward over a second portion of the range, the second portion corresponding to longer VT intervals; and a multiplier for multiplying the cardiac interval with the coupling percentage to obtain a corresponding coupling interval, the coupling interval changing nonlinearly with respect to the cardiac interval as a result of the multiplication; and a therapy generator for generating the antitachycardia therapy, the antitachycardia therapy being applied after a cardiac beat characteristic of the tachycardia, with the duration between the cardiac beat and the antitachycardia therapy being defined by the coupling interval.

16. The cardioverter/defibrillator of claim 15, wherein the coupling percentage generator defines a first predetermined range and a second predetermined range for the cardiac interval, the coupling percentage changing linearly with the cardiac interval for the first predetermined range, and the coupling interval remaining constant for the second predetermined interval.

17. The cardioverter/defibrillator of claim 16, wherein the coupling interval changes nonlinearly with the cardiac interval for the first predetermined range and changes linearly with the cardiac interval during the second predetermined range.

18. In an implantable cardiac stimulation device arranged and constructed to provide antitachycardia therapy to a patient's heart, a method of determining the coupling interval comprising the steps of:

detecting pathological tachycardia having a VT interval within a predetermined range;

generating a dynamically adjustable coupling interval based on a non-linear function of the VT interval so that a more proportionately aggressive therapy is applied as the VT interval gets longer; and generating a sequence of antitachycardia stimulation pulses so that at least a first stimulation pulse following a VT interval occurs after the coupling interval.

* * * * *